(12) United States Patent
Lee et al.

(10) Patent No.: US 6,719,702 B2
(45) Date of Patent: Apr. 13, 2004

(54) APPARATUS AND METHOD FOR MEASURING BLOOD PRESSURE USING LINEARLY VARYING AIR PRESSURE

(75) Inventors: Jong-youn Lee, Seoul (KR); Gil-won Yoon, Seoul (KR)

(73) Assignee: Samsung Electronics Co., Ltd., Kyungki-do (KR)

( * ) Notice: Subject to any disclaimer, the term of this patent is extended or adjusted under 35 U.S.C. 154(b) by 52 days.

(21) Appl. No.: 10/155,136

(22) Filed: May 28, 2002

(65) Prior Publication Data

US 2003/0060720 A1 Mar. 27, 2003

(30) Foreign Application Priority Data

Aug. 21, 2001 (KR) ................. 10-2001-0050321

(51) Int. Cl.[7] ................................................. A61B 5/02
(52) U.S. Cl. ..................... 600/490; 600/493; 600/494
(58) Field of Search ................... 600/481, 485, 600/490, 493, 494, 495, 496

(56) References Cited

U.S. PATENT DOCUMENTS

| | | | |
|---|---|---|---|
| 4,567,899 A | * | 2/1986 | Kamens et al. ............. 600/493 |
| 4,889,132 A | * | 12/1989 | Hutcheson et al. ......... 600/493 |
| 5,038,790 A | * | 8/1991 | Malkamaki ................. 600/490 |
| 5,579,776 A | | 12/1996 | Medero |
| 5,660,182 A | | 8/1997 | Kuroshaki et al. |
| 6,171,254 B1 | * | 1/2001 | Skelton ....................... 600/490 |

FOREIGN PATENT DOCUMENTS

| | | |
|---|---|---|
| EP | 0 353 315 A1 | 2/1990 |
| KR | 96-3683 | 2/1996 |

* cited by examiner

Primary Examiner—Max F. Hindenburg
Assistant Examiner—Navin Natnithithadha
(74) Attorney, Agent, or Firm—Lee & Sterba, P.C.

(57) ABSTRACT

An apparatus and method for measuring blood pressure using linearly varying air pressure, including a compression unit; an air pump that injects air into the compression unit; a pressure sensor that senses and outputs the air pressure of the compression unit; an ADC that converts and outputs the result of the sensing as a pressure signal; a controller that calculates a current pressure value of the compression unit from the pressure signal and a linear pressure of the compression unit that is linearly dropped corresponding to the current pressure value and generates the first control signal in response to the current pressure value and a second control signal from the result of a comparison of the current pressure value and the linear pressure; a DAC that converts and outputs the second control signal as an exhaust control signal; and a proportional control valve that exhausts air from the compression unit.

11 Claims, 6 Drawing Sheets

APPARATUS AND METHOD FOR MEASURING BLOOD PRESSURE USING LINEARLY VARYING AIR PRESSURE

BACKGROUND OF THE INVENTION

1. Field of the Invention

The present invention relates to the measurement of blood pressure. More particularly, the present invention relates to an apparatus and method for measuring blood pressure using linearly varying air pressure.

2. Description of the Related Art

Blood pressure is the most useful, easy-to-measure index among a variety of indices of the health of a human being. Blood pressure is used as an index for diagnosing disorders of the circulatory system including the heart and blood vessels. Additionally, when blood pressure is above a normal range, particular medical treatments may be required.

Arterial blood pressure fluctuates due to the beating of the heart. The blood pressure at a period of time during which blood is discharged into the artery due to contraction of the ventricle of the heart is called the "systolic blood pressure." The blood pressure at a period of time during which no blood is discharged into the artery due to extension of the ventricle, but where blood pressure is maintained above zero due to the elasticity of the arterial blood vessel, is called the "diastolic blood pressure."

Blood pressure varies with many factors. Accordingly, it is difficult to measure blood pressure accurately through only a single measurement. For example, when a blood pressure measurement is taken in a hospital, false hypertension often occurs due to the stress of a patient and results in an accurate reading.

Blood pressure that is measured in the morning, before eating, is referred to as "basal blood pressure." Basal blood pressure is critical for diagnostic purposes, but is difficult to accurately measure under ideal conditions. In order to measure the basal blood pressure as accurately as possible, under near ideal conditions, blood pressure must be measured at home. To facilitate the measurement of basal blood pressure, there is an increasing need for an electronic blood pressure monitor that enables a person to measure blood at home easily.

Research has been conducted in a variety of aspects to enable people to accurately measure their blood pressure at home. In particular, due to the advances in the electronics industry, automated blood pressure monitors, with which human blood pressure can be indirectly measured, have become available. One automated blood pressure monitor in current use is based on a volume oscillometric method that requires no particular transducer or microphone.

It is assumed that there is a predetermined characteristic ratio between the cuff oscillation magnitudes during systolic and diastolic cycles with respect to the maximum oscillation magnitude of the cuff. In a conventional blood pressure measuring method using an arterial blood pressure pulsation measuring apparatus the blood pressure measured under the cuff oscillation condition inducing about 50% of the maximum cuff oscillation magnitude is estimated as the "systolic blood pressure," and the blood pressure measured under the cuff oscillation condition inducing about 50–80% of the maximum cuff oscillation magnitude is estimated as the "diastolic blood pressure." These conclusions were obtained through trials conducted on human beings and dogs.

Figure 1:
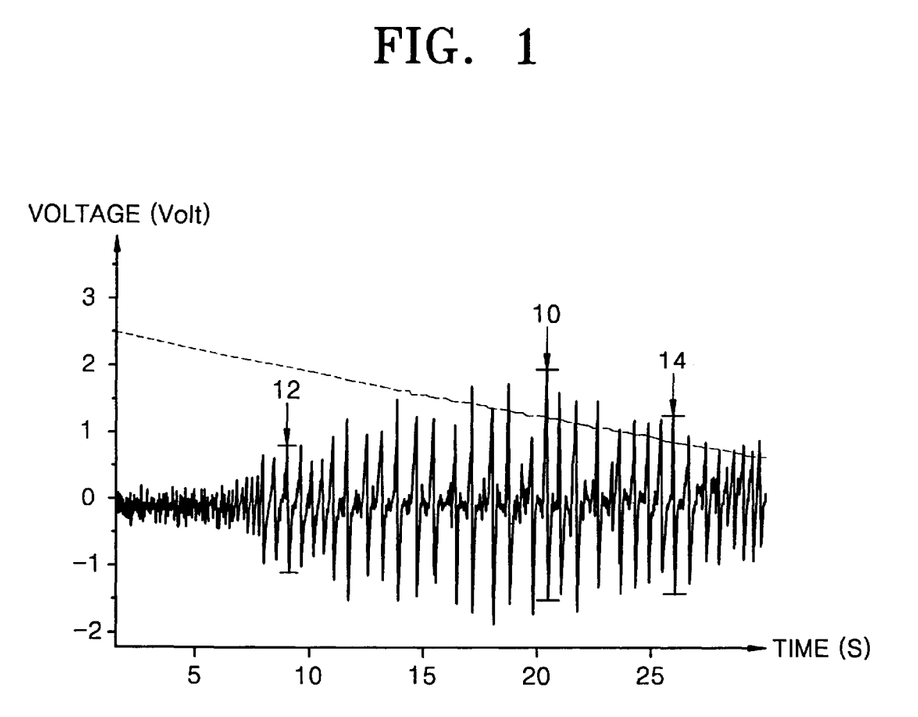
FIG. 1 is a graph showing a pressure signal of the cuff and a volume oscillometric signal.

FIG. 1 is a graph showing a pressure signal of the cuff and a volume oscillometric signal, in which the pressure signal is denoted by the dashed line and the volume oscillometric signal is denoted by the solid line.

The pressure signal of FIG. 1 appears as the pressure of the cuff is linearly reduced. The volume oscillometric signal of FIG. 1 is obtained by passing the pressure signal through a 0.5 Hz high-pass filter and amplifying the filtered pressure signal. As the pressure of the cuff is reduced at a constant rate, the maximum amplitude 10 of the volume oscillometric signal occurs at a cuff pressure for the average blood pressure. The systole amplitude 12 corresponding to 50% of the maximum amplitude 10 is read as the systolic blood pressure. The diastole amplitude 14 corresponding to 75% of the maximum amplitude 10 is read as the diastolic blood pressure. The ratios of the systole amplitude 12 and the diastole amplitude 14 to the maximum amplitude 10 are referred to as the "characteristic ratios." These characteristic ratios have a variation of 10–20% depending on the individual being measured and are affected considerably by the appearance and elasticity of the cuff, the shape and amplitude of the arterial pressure waveform, and a variety of vital dynamical factors including the pressure transfer characteristics of the artery, the arm, and the cuff, and the viscoelastic characteristics of the arterial blood vessel.

Most blood pressure measuring apparatuses in current use measure blood pressure at the brachium (i.e., the upper arm). Accordingly, in preparation for a blood pressure measurement, an individual faces the inconvenience of taking off his/her jacket and rolling up a shirtsleeve. Additionally, a relatively high pressure is applied several times during the measurement of blood pressure, which may cause discomfort for the individual.

Air pressure valves typically have nonlinear exhaust characteristics. This is especially true in a finger type cuff having a small-capacity air bag, where the exhaust characteristics tend to be even more nonlinear. If the air pressure of the cuff is reduced nonlinearly, then the maximum oscillation is affected. Therefore, such a conventional blood pressure measuring apparatus is not able to measure blood pressure accurately.

SUMMARY OF THE INVENTION

In an effort, to solve the above-described problems, it is a first feature of an embodiment of the present invention to provide a blood pressure measuring apparatus capable of measuring blood pressure using linearly varying air pressure and which is conveniently applied to an individual having a blood pressure measurement taken.

It is a second feature of an embodiment of the present invention to provide a method for measuring blood pressure using linearly varying air pressure in the blood pressure measuring apparatus described above.

To provide the first feature of an embodiment of the present invention, there is provided an apparatus for measuring blood pressure using linearly varying air pressure, including: a compression unit to be applied to surround a predetermined site of an individual's body, the compression unit being inflatable and deflatable; an air pump that injects air into the compression unit in response to a first control signal; a pressure sensor that senses the air pressure of the compression unit and outputs the result of the sensing; an analog-to-digital converter (ADC) that converts the result of the sensing from an analog form into a digital form and outputs the result of the conversion as a pressure signal; a controller that calculates a current pressure value of the compression unit from the pressure signal and a linear pressure of the compression unit that is linearly dropped corresponding to the calculated current pressure value, generates the first control signal in response to the current pressure value, and generates a second control signal from the result of a comparison of the current pressure value and the linear pressure to measure the blood pressure of the individual; a digital-to-analog converter that converts the second control signal into an analog form and outputs the result of the conversion as an exhaust control signal; and a proportional control valve that exhausts air from the compression unit in response to the exhaust control signal.

To provide the second feature of an embodiment of the present invention, there is provided a method for measuring an individual's blood pressure using linearly varying air pressure including: (a) injecting air into a compression unit until a reference pressure value is reached; (b) calculating a current pressure value of the compression unit from a pressure signal output from an analog-to-digital converter (ADC), and a linear pressure for the current pressure value; (c) determining whether the current pressure value is greater than the linear pressure; (d) if the current pressure value is determined to be greater than the linear pressure, increasing a rate of dropping pressure of the compression unit; (e) if the current pressure value is determined to be equal to or less than the linear pressure, decreasing the rate of dropping pressure of the compression unit; (f) after (d) or (e), determining whether a number of current pressure values calculated is equal to $f_s \times t$, where $f_s$ denotes a sampling frequency of the analog-to-digital converter and t denotes a period of time required until a maximum pressure $P_{max}$ of the compression unit drops to a minimum pressure $P_{min}$; (g) if the number of current pressure values is determined to be less than $f_s \times t$, then changing a variable i denoting the order of the pressure signal input from the analog-to-digital converter, and proceeding to (b); and (h) if the number of current pressure values is determined to be equal to $f_s \times t$, determining the blood pressure using the current pressure values in a quantity equal to $f_s \times t$.

BRIEF DESCRIPTION OF THE DRAWINGS

The above features and advantages of the present invention will become more apparent by describing in detail preferred embodiments thereof with reference to the attached drawings in which.

DETAILED DESCRIPTION OF THE INVENTION

Korean Patent Application No. 2001-50321, filed on Aug. 21, 2001, and entitled: "Apparatus and Method for Measuring Blood Pressure Using Linearly Varying Air Pressure," is incorporated by reference herein in its entirety.

The structure and operation of a blood pressure measuring apparatus using linearly varying air pressure according to the present invention will be described with reference to the appended drawings.

Figure 2:
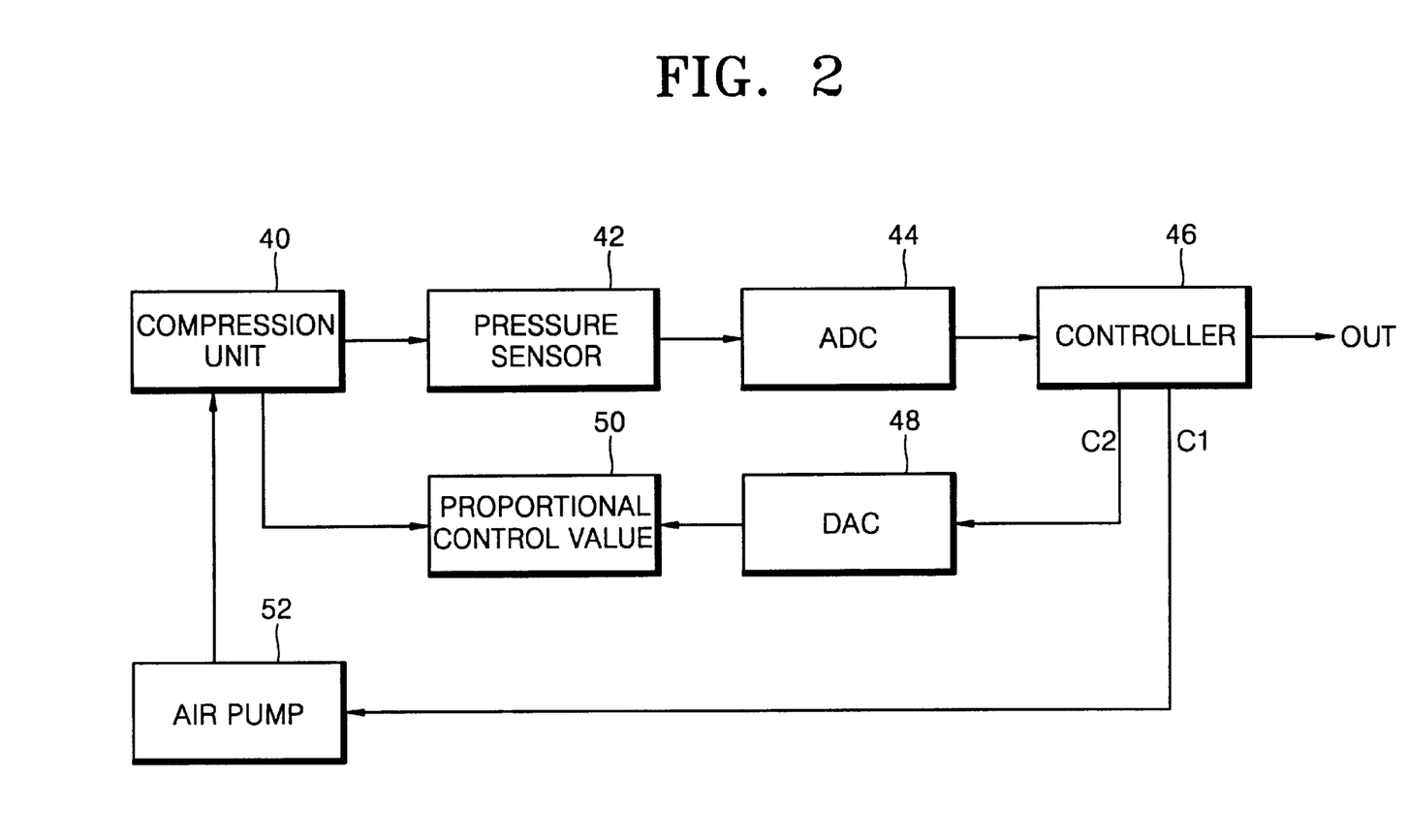
FIG. 2 illustrates a block diagram of a blood pressure measuring apparatus using linearly varying air pressure according to the present invention.

FIG. 2 illustrates a block diagram of a blood pressure measuring apparatus using linearly varying blood pressure according to the present invention. The blood pressure measuring apparatus includes a compression unit 40, a pressure sensor 42, an analog-to-digital converter (ADC) 44, a controller 46, a digital-to-analog converter (DAC) 48, a proportional control valve 50, and an air pump 52.

The compression unit 40 of FIG. 2 is inflatable and deflatable and is applied to surround a predetermined site of an individual's body. The predetermined site of the body may be a finger, an arm, a leg, a toe, etc. The structure and operation of a preferred embodiment of the compression unit 40 according to the present invention will now be described in greater detail with reference to the appended drawings.

Figure 3:
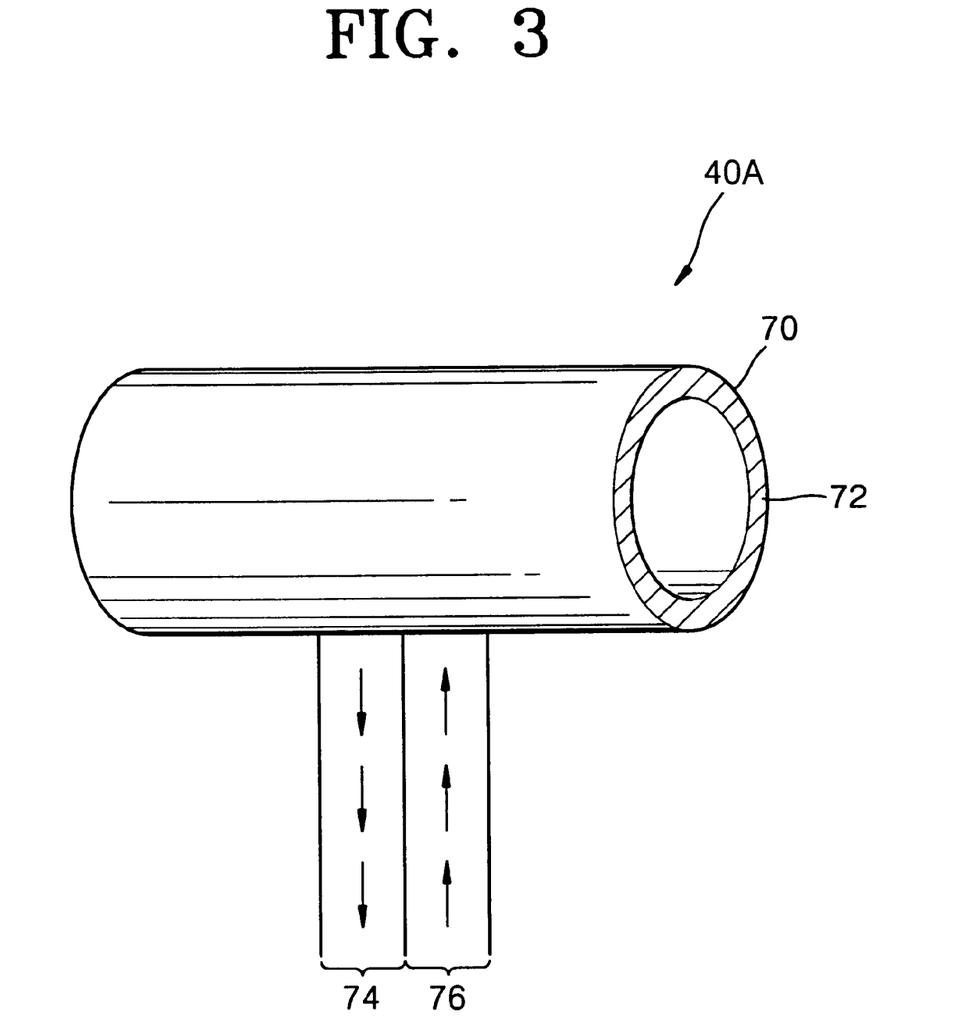
FIG. 3 shows the appearance of a preferred embodiment of a compression unit of the blood pressure measuring apparatus according to the present invention.

FIG. 3 shows the appearance of a preferred embodiment 40A of the compression unit 40 of FIG. 2 according to the present invention. The compression unit 40A includes an air bag 72, an outlet tube 74, and an inlet tube 76. Referring to FIG. 3, the inlet tube 76 of the compression unit 40A allows air entering from the air pump 52 to flow into the air bag 72, as shown by the arrows pointing up. An outlet tube 74 exhausts the air in the air bag 72 into the proportional control valve 50, as shown by the arrows pointing down. The air bag 72 to be applied to surround a predetermined site of the body is connected to the inlet tube 76 and the outlet tube 74 so that air can flow into and out of the air bag 72. The air bag 72 may be implemented with a flexible deflatable and inflatable material, such as rubber. The outer coat 70 of the air bag 72 may be implemented with a cylindrical rigid material.

Unlike the embodiment shown in FIG. 3, in another embodiment of the present invention, the compression unit 40 may be implemented to have a single tube (not shown) through which air enters from the air pump 52 and exhausts into the proportional control valve 50. In other words, the inlet tube 76 and the outlet tube 74, which are illustrated in FIG. 3 as separated from each other, may be combined, if necessary, into a single tube through which air inflow or exhaust is performed.

The time required for the compression unit 40A to reach a predetermined reference pressure value varies according to the circumference of the air bag 72, which changes according to the girth of a predetermined site of the body. The circumference of the air bag 72 varies depending on the amount of air entering from the air pump 52 or the amount of air exhausted into the proportional control valve 50. Here, the compression unit 40A, which is cylindrical, must be large enough to surround a predetermined site of the body to be measured.

The air pump 52 of FIG. 2 acts to inject air into the compression unit 40 in response to a first control signal C1 input from the controller 46. Here, the pressure sensor 42 senses the pressure of the compression unit 40 and outputs the result of the sensing to the ADC 44. The ADC 44 converts the result of the sensing from an analog form, which was input from the compression sensor 42, into a digital form and outputs the result of the conversion to the controller 44 as a pressure signal.

The controller 46 calculates a current pressure value $P_c$ of the compression unit 40 from the digital pressure signal input from the ADC 44, calculates a linear pressure P(i) linearly dropped corresponding to the calculated current pressure value $P_c$ of the compression unit 40 using formula (1) below, and generates the first control signal C1 in response to the calculated current pressure value $P_c$:

$$P(i) = P_{max} - \frac{P_{max} - P_{min}}{f_s \times t} \times i \qquad (1)$$

where $P_{max}$ and $P_{min}$ denote the predetermined maximum and minimum pressures of the compression unit 40, respectively, $f_s$ denotes a predetermined sampling frequency of the ADC 44, t denotes a predetermined period of time required until the maximum pressure $P_{max}$ drops to the minimum pressure $P_{min}$, and i denotes the order of the pressure signal input from the ADC 44, where $0 \leq i \leq f_s \times t$.

The controller 46 may include a counter (not shown) which counts up or count down from zero to $f_s \times t$ in ascending or descending order and outputs the result of the counting as variable i. The controller 46 generates a second control signal C2 from the result of a comparison of the current pressure value $P_c$ and the linear pressure P(i) and outputs the second control signal C2 to the DAC 48. The controller 46 measures the blood pressure of the individual from the current pressure value $P_c$ and outputs the measured blood pressure through an output port OUT. The controller 46 may include an additional memory (not shown) for storing the current pressure value $P_c$ calculated from pressure signals successively input from the ADC 44. In this case, the controller 46 reads out the current pressure value $P_c$ stored in the memory and determines the blood pressure of the individual from the current pressure value $P_c$.

According to the present invention, the controller 46 can measure the time required until the air pressure of the compression unit 40 reaches a predetermined level, using the pressure signal input from the ADC 44, and determines the blood pressure using the measured time and the current pressure value $P_c$ calculated using the pressure signals successively input from the ADC 44 and stored in the memory. The controller 46 indirectly measures the circumference of the compression unit 40 using the time required until the air pressure of the compression unit reaches the predetermined level and reflects the measured time on the characteristic ratio described above in measuring the blood pressure using an oscillometric method.

The DAC 48 converts the second control signal C2 input from the controller 46 into an analog form and outputs the result of the conversion to the proportional control valve 50 as an exhaust control signal. The proportional control valve 50 controls the amount of air to be exhausted from the compression unit 40 in response to the exhaust control signal input from the DAC 48.

Hereinafter, a blood pressure measuring method performed in the blood pressure measuring apparatus shown in FIG. 2 using linearly varying air pressure according to the present invention will be described with reference to the appended drawings.

Figure 4:
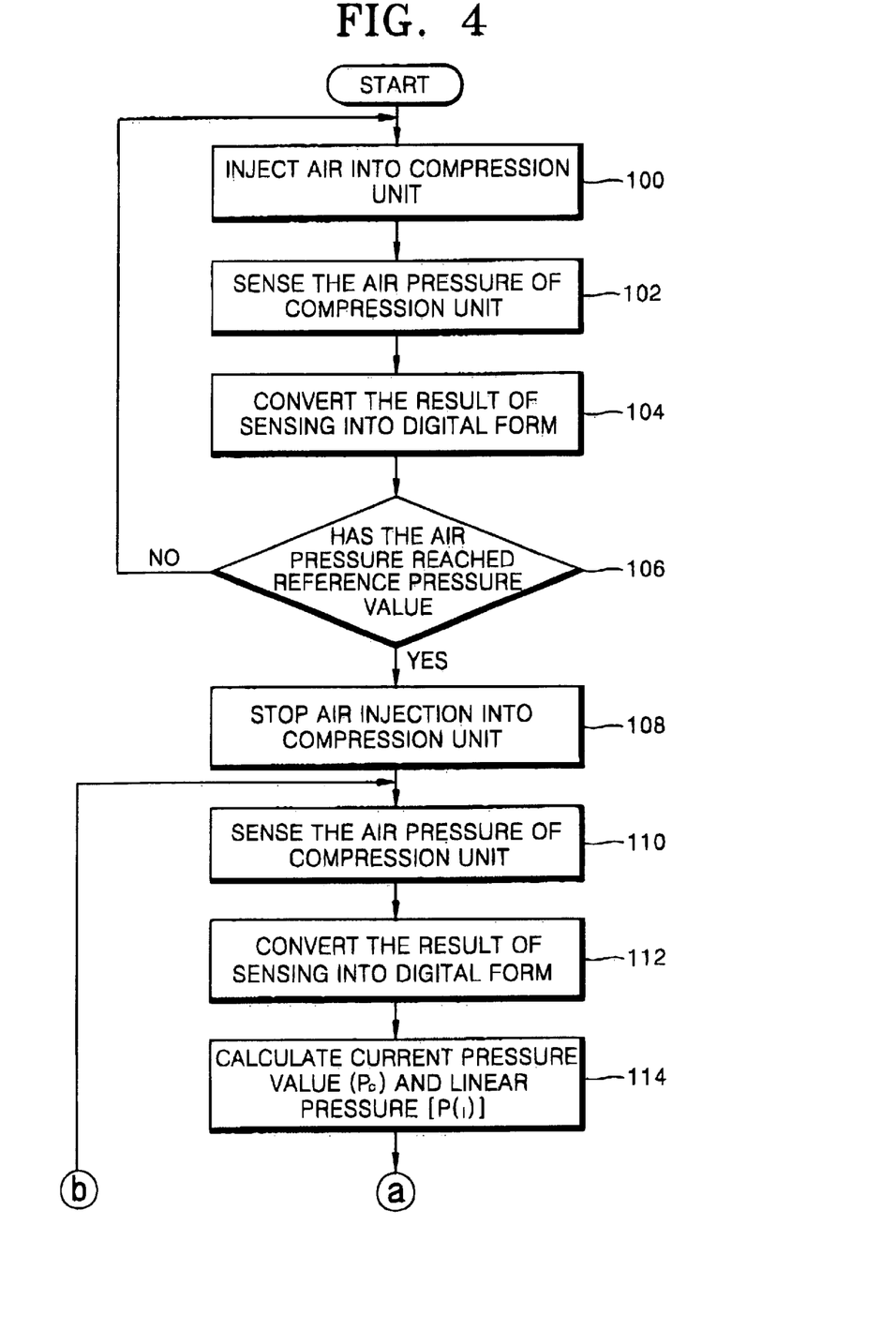
FIG. 4 is a flowchart illustrating a blood pressure measuring method using linearly varying air pressure according to the present invention.

FIG. 4 is a flowchart illustrating an embodiment of the blood pressure measuring method using linearly varying air pressure according to the present invention. The blood pressure measuring method of FIG. 4 involves injecting air into the compression unit 40, in steps 100 through 108, calculating the current pressure value $P_c$ and the linear pressure P(i) of the compression unit 40, in steps 110 through 114, adjusting a rate of dropping pressure of the compression unit 40 according to the difference between the calculated current pressure value $P_c$ and linear pressure P(i), in steps 116 through 120, and changing variable i depending on the number of current pressure values $P_c$ that have been calculated or determining the blood pressure, in steps 122 through 126.

In steps 100 through 108, in the blood pressure measuring method according to the present invention, first the compression unit 40 having the air bag 72 containing air under atmospheric pressure is applied to surround a predetermined site of the body, and air is injected into the compression unit 40 to a predetermined reference pressure value using the air pump 52. In particular, in step 100, the air pump 52 injects air into the compression unit 40. After step 100, in step 102, the compression sensor 42 senses the air pressure of the compression unit 40 and outputs the result of the sensing to the ADC 44. After step 102, in step 104, the ADC 44 converts the result of the sensing from the pressure sensor 42 into a digital form to obtain a pressure signal. After step 104, in step 106, the controller 46 determines whether the air pressure of the compression unit 40 has reached the reference pressure value from the pressure signal input from the ADC 44. If the air pressure of the compression unit 40 is determined not to have reached the reference pressure value, then the returns proceeds to step 100. In other words, if the air pressure of the compression unit 40 is determined not to have reached the reference pressure value, then the controller 46 generates the first control signal C1 to control the air pump 52 so that the air pump 52 continues to supply air to the compression unit 40. Alternatively, in step 108, if it is determined from the pressure signal that the air pressure of the compression unit 40 has reached the reference pressure value, then the controller 46 stops the air pump 52 from supplying air to the compression unit 40 using the first control signal C1.

Once the air pressure of the compression unit 40 reaches the reference pressure value and the injection of air from the air pump 52 to the compression unit 40 is stopped, the compression unit 40 begins to exhaust air. After step 108, in steps 110 through 114, the controller 46 calculates the current pressure value $P_c$ of the compression unit 40 and the linear pressure P(i) for the current pressure value $P_c$ using formula (1) above. In particular, after step 108, in step 110, the compression sensor 42 senses the air pressure of the compression unit 40 dropping from the maximum pressure $P_{max}$ as air is exhausted from the compression unit 40. After step 110, in step 112, the ADC 44 converts the result of the sensing from the pressure sensor 42 into a digital form to obtain a pressure signal. After step 112, in step 114, the controller 46 calculates the current pressure value $P_c$ using the pressure signal input from the ADC 44 and the linear pressure P(i) for the current pressure value $P_c$.

After step 114, in step 116, the controller 46 determines whether the current pressure value $P_c$ is greater than the linear pressure P(i). In step 118, if the current pressure value $P_c$ is determined to be equal to or less than the linear pressure P(i), the controller 46 reduces the rate of dropping pressure of the compression unit 40. To this end, if the current pressure value $P_c$ is determined not to be greater than the linear pressure P(i), the controller 46 generates a second control signal C2 that decreases the orifice of the proportional control valve 50, so that the amount of air exhausted from the compression unit 40 decreases with the proportional control valve 50. Alternatively, in step 120, if the current pressure $P_c$ is determined to be greater than the linear pressure P(i), the controller 46 increases the rate of dropping pressure of the compression unit 40. To this end, if the current pressure value $P_c$ is determined to be greater than the linear pressure P(i), the controller 46 generates a second control signal C2 that increases the orifice of the proportional control valve 50, so that the amount of air exhausted from the compression unit 40 increases with the proportional control value 50.

After step 118 or step 120, in step 122, the controller 46 determines whether the number of current pressure values $P_c$ that have been calculated is equal to $f_s \times t$. If the counter described above performs up-counting, the controller 46 determines whether $i = f_s \times t$. If the counter described above performs down-counting, the controller 46 determines whether $i = 0$.

In step 124, if the number of current pressure values $P_c$ that have been calculated is determined to be less than $f_s \times t$, the controller 46 increases (or decreases) variable i by 1 and returns to step 110. For example, if the linear pressure P(i) is calculated starting with $i = 0$ in step 114, that is, if the counter provided for the controller 46 performs up-counting, the controller 46 increases variable i by 1. Alternatively, if the linear pressure P(i) is calculated starting with $i = f_s \times t$ in step 114, that is, if the counter provided for the controller 46 performs down-counting, the controller 46 decreases variable i by 1.

In step 126, if the number of current pressure values $P_c$ that have been calculated is determined to be equal to $f_s \times t$, the controller 46 measures the blood pressure using the current pressure values $P_c$ stored in the memory and in a quantity equal to $f_s \times t$.

Non-linear and linear pressure dropping characteristics of the compression unit 40 of FIG. 2 will now be compared with reference to the appended drawings.

Figure 5:
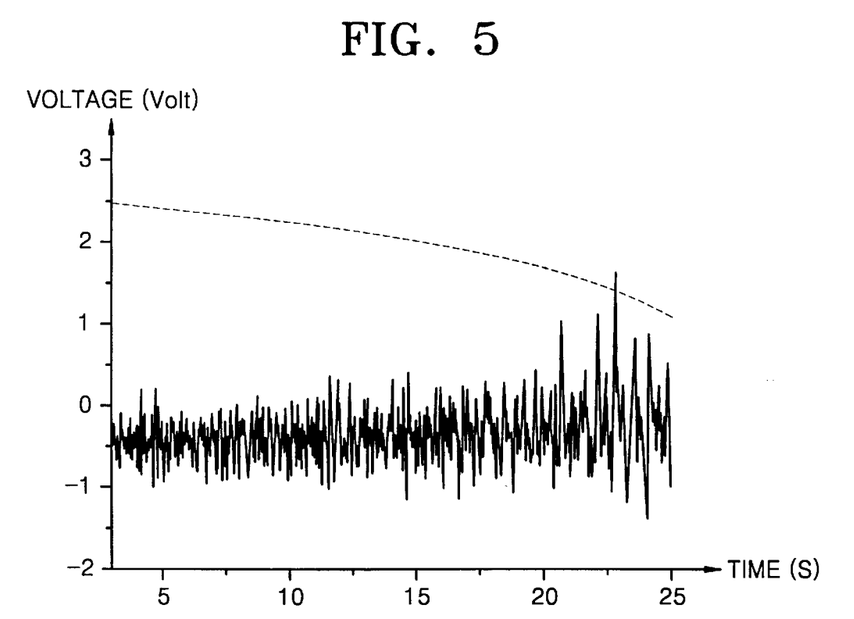
FIG. 5 is a graph illustrating nonlinear pressure dropping characteristics.

FIG. 5 is a graph illustrating the non-linear pressure dropping characteristics of the compression unit 40. In FIG. 5, the vertical axis represents voltage and the horizontal axis represents time. A pressure signal is denoted by the dashed line and a volume oscillometric signal is denoted by the solid line.

Figure 6:
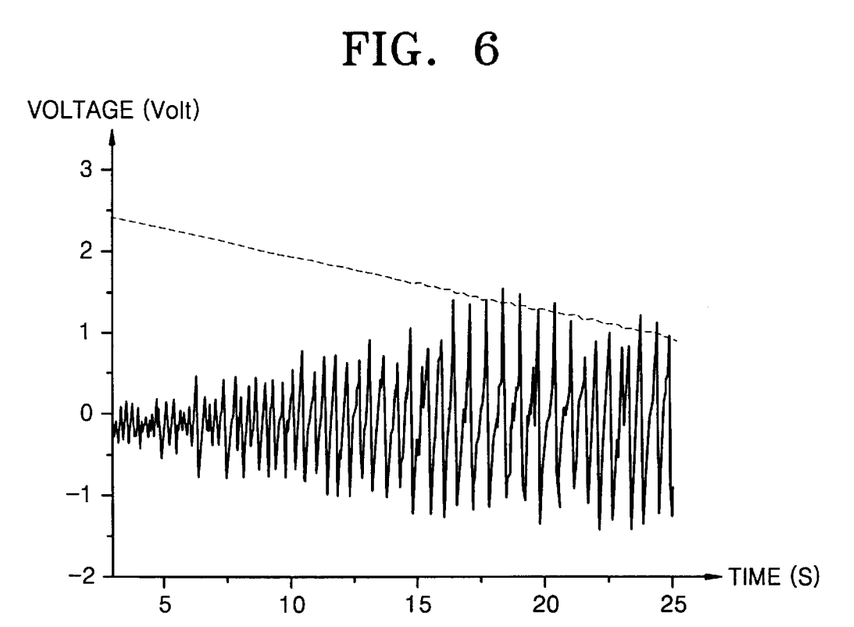
FIG. 6 is a graph illustrating linear pressure dropping characteristics.

FIG. 6 is a graph illustrating the linear pressure dropping characteristics of the compression unit 40. In FIG. 6, the vertical axis represents voltage and the horizontal axis represents time.

As shown in FIG. 5, when the air pressure of the compression unit 40 drops nonlinearly, it is difficult to identify the maximum and minimum pressures of the compression unit 40. When the air pressure of the compression unit 40 linearly drops, however, as shown in FIG. 6, as in the blood pressure measuring apparatus and method according to the present invention, the maximum and minimum pressures of the compression unit 40 may be clearly identified.

The blood pressure was measured for 8 human subjects 10 times using the blood pressure measuring apparatus and method according to the present invention and a conventional auscultatory method. The results are shown in Table 1.

TABLE 1

| Subject No. | Present Invention | | Auscultatory Method | | Mean Error | |
|---|---|---|---|---|---|---|
| | Mean/SD of SBP | Mean/SD of DBP | Mean/SD of SBP | Mean/SD of DBP | SBP | DBP |
| 1 | 109/3 | 72/2 | 108/2 | 72/2 | 1 | 0 |
| 2 | 101/8 | 69/9 | 103/2 | 64/2 | 2 | 5 |
| 3 | 107/13 | 61/4 | 103/3 | 57/3 | 4 | 4 |
| 4 | 114/5 | 63/5 | 112/5 | 69/3 | 2 | 6 |
| 5 | 100/5 | 66/4 | 107/2 | 61/2 | 7 | 5 |
| 6 | 115/5 | 80/5 | 109/3 | 74/1 | 6 | 6 |
| 7 | 102/3 | 57/5 | 93/1 | 59/1 | 9 | 2 |
| 8 | 107/10 | 77/6 | 104/1 | 66/1 | 0 | 13 |
| | | | | | 3.8 | 5.1 |
| MSD | 6.5 | 5 | 2.4 | 1.8 | | |

SBP: Systolic Blood Pressure; DBP: Diastolic Blood Pressure; SD: Standard Deviation; MSD: Mean Standard Deviation The mean error of the systolic blood pressure (SBP) refers to the difference between the mean SBP levels measured using the blood pressure measuring apparatus and method according to the present invention and the auscultatory method. The mean error of the diastolic blood pressure (DBP) refers to the difference between the mean DBP levels measured using the blood pressure measuring apparatus and method according to the present invention and the auscultatory method. As may be seen in Table 1, the blood pressure determining apparatus and method according to the present invention meet a mean error requirement of ±5 mmHg for electronic medical equipment as suggested by, for example, the Korea Food and Drug Administration.

As described above, in the apparatus and method using linearly varying air pressure to measure blood pressure according to the present invention, the cuff may be applied to any site of the body, such as a finger, other than the brachial artery. Accordingly, the individual is not required to take off his/her jacket and roll up a shirtsleeve, so that the individual can measure his/her blood pressure conveniently several times. In addition, because the air pressure of the compression unit after being injected with air can be linearly dropped without affecting the maximum oscillation, the blood pressure of the individual can be accurately measured.

While the present invention has been particularly shown and described with reference to preferred embodiments thereof, it will be understood by those of ordinary skill in the art that various changes in form and details may be made therein without departing from the spirit and scope of the present invention as defined by the appended claims.

What is claimed is:

1. An apparatus for measuring blood pressure using linearly varying air pressure, comprising:

a compression unit to be applied to surround a predetermined site of an individual's body, the compression unit being inflatable and deflatable;

an air pump that injects air into the compression unit in response to a first control signal;

a pressure sensor that senses the air pressure of the compression unit and outputs the result of the sensing;

an analog-to-digital converter (ADC) that converts the result of the sensing from an analog form into a digital form and outputs the result of the conversion as a pressure signal;

a controller that calculates a current pressure value of the compression unit from the pressure signal and a linear pressure of the compression unit that is linearly dropped corresponding to the calculated current pressure value, generates the first control signal in response to the current pressure value, and generates a second control signal from the result of a comparison of the current pressure value and the linear pressure to measure the blood pressure of the individual;

a digital-to-analog converter that converts the second control signal into an analog form and outputs the result of the conversion as an exhaust control signal; and a proportional control valve that exhausts air from the compression unit in response to the exhaust control signal.

2. The apparatus as claimed in claim 1, wherein the predetermined site of the individual's body is a finger.

3. The apparatus as claimed in claim 1, wherein the compression unit comprises:

an inlet tube through which air from the air pump enters the compression unit;

an outlet tube through which air is exhausted from the compression unit;

an air bag, which is inflatable or deflatable, is applied to surround the predetermined site of the individual's body, and is connected to the inlet tube which takes in air and to the outlet tube which exhausts air, wherein the time required for the air bag to reach a reference pressure value varies based on the circumference of the air bag changing according to the girth of the predetermined site.

4. The apparatus as claimed in claim 1, wherein the compression unit comprises:

a tube through which air from the air pump enters the compression unit or air is exhausted from the compression unit into the proportional control valve; and an air bag which is inflatable or deflatable, is applied to surround the predetermined site of the individual's body, and is connected to the inlet tube which takes in air and to the outlet tube which exhausts air, wherein the time required for the air bag to reach a reference pressure value varies based on the circumference of the air bag changing according to the girth of the predetermined site.

5. The apparatus as claimed in claim 1, wherein the controller calculates the linear pressure P(i) using the formula below:

$$P(i) = P_{max} - \frac{P_{max} - P_{min}}{f_s \times t} \times i$$

where $P_{max}$ and $P_{min}$ denote the predetermined maximum and minimum pressures of the compression unit, respectively, $f_s$ denotes a predetermined sampling frequency of the analog-to-digital converter, t denotes a period of time required until the maximum pressure $P_{max}$ drops to the minimum pressure $P_{min}$, and i denotes the order of the pressure signal input from the analog-to-digital converter in the range of $0 \leq i \leq f_s \times t$.

6. The apparatus as claimed in claim 1, wherein the controller measures the time required for the compression unit to reach a predetermined pressure level using the pressure signal, and measures the blood pressure using the measured time and the current pressure value.

7. A method for measuring the blood pressure using linearly varying air pressure, comprising:

(a) injecting air into a compression unit until a reference pressure value is reached;

(b) calculating a current pressure value of the compression unit from a pressure signal output from an analog-to-digital converter (ADC), and a linear pressure for the current pressure value;

(c) determining whether the current pressure value is greater than the linear pressure;

(d) if the current pressure value is determined to be greater than the linear pressure, increasing a rate of dropping pressure of the compression unit;

(e) if the current pressure value is determined to be equal to or less than the linear pressure, decreasing the rate of dropping pressure of the compression unit;

(f) after (d) or (e), determining whether a number of current pressure values calculated is equal to $f_s \times t$, where $f_s$ denotes a sampling frequency of the analog-to-digital converter and t denotes a period of time required until a maximum pressure $P_{max}$ of the compression unit drops to a minimum pressure $P_{min}$;

(g) if the number of current pressure values is determined to be less than $f_s \times t$, then changing a variable i denoting the order of the pressure signal input from the analog-to-digital converter and proceeding to (b); and (h) if the number of current pressure values is determined to be equal to $f_s \times t$, determining the blood pressure using the current pressure values in a quantity equal to $f_s \times t$.

8. The method as claimed in claim 7, wherein (a), injecting air into the compression unit, comprises:

(a1) injecting air into the compression unit;

(a2) sensing the air pressure of the compression unit;

(a3) converting a result of the sensing into a digital form to obtain a pressure signal;

(a4) determining whether the air pressure of the compression unit reaches the reference pressure value from the pressure signal and if the air pressure of the compression unit is determined not to reach the reference pressure value, proceeding to (a1); and (a5) if the air pressure is determined to reach the reference pressure value, stopping the injection of air into the compression unit and proceeding to (b).

9. The method as claimed in claim 7, wherein (b), calculating the current pressure value and the linear pressure, comprises:

(b1) after (a), sensing the air pressure of the compression unit;

(b2) converting a result of the sensing into a digital form to obtain the pressure signal; and (b3) calculating the current pressure value using the pressure signal and the linear pressure for the current pressure and proceeding to (c).

10. The method as claimed in claim 7, wherein if the linear pressure is calculated starting with i=0 in (b) and the number of current pressure values calculated is determined to be less than $f_s \times t$ in (f), then the variable i is increased by 1 in (g), and the process proceeds to (b), and if the linear pressure is calculated starting with $i=f_s \times t$ in (b) and the number of current pressure values calculated is determined to be less than $f_s \times t$ in (f), then the variable i is decreased by 1 in (g), and the process proceeds to (b).

11. The method as claimed in claim 7, wherein (h) comprises measuring the time required for the compression unit to reach a predetermined pressure level and determining the blood pressure using the measured time and the current pressure values.

* * * * *